United States Patent [19]
Dhadwal et al.

[11] Patent Number: 5,627,642
[45] Date of Patent: May 6, 1997

[54] METHOD AND APPARATUS FOR SUBMICROSCOPIC PARTICLE SIZING BY MEASURING DEGREE OF COHERENCE

[75] Inventors: Harbans S. Dhadwal, Setauket, N.Y.; Kwang I. Suh, Strongville, Ohio

[73] Assignee: The Research Foundation of State University of New York, Albany, N.Y.

[21] Appl. No.: 514,264

[22] Filed: Aug. 11, 1995

[51] Int. Cl.⁶ .................................................. G01N 15/02
[52] U.S. Cl. ............................................................ 356/336
[58] Field of Search ................................... 356/336, 337, 356/338

[56] References Cited

U.S. PATENT DOCUMENTS

| | | |
|---|---|---|
| 4,701,011 | 10/1987 | Emkey et al. . |
| 4,801,205 | 1/1989 | Tatsuno . |
| 4,830,494 | 5/1989 | Ishikawa et al. . |
| 4,975,237 | 12/1990 | Brown . |
| 4,983,040 | 1/1991 | Chu et al. . |
| 5,015,094 | 5/1991 | Oka et al. . |
| 5,155,549 | 10/1992 | Dhadwal . |
| 5,257,087 | 10/1993 | Furuya . |
| 5,284,149 | 2/1994 | Dhadwal et al. . |

OTHER PUBLICATIONS

Dhadwal, et al., "Integrated Fiber Optic Probe for Dynamic Light Scattering," *Applied Optics*, vol. 32, No. 21, pp. 3901–3904 (1993).

D. Slepian, "Fluctuations of Random Noise Power," *The Bell System Technical Journal*, pp. 163–184 (1958).

Jakeman, et al., "The Intensity–Fluctuation Distribution of Gaussian Light," *J. Phys. A (Proc. Phys. Soc.)*, vol. 1, Ser. 2, pp. 128–138 (1968).

*Primary Examiner*—Georgia Y. Epps
*Assistant Examiner*—Amanda Merlino
*Attorney, Agent, or Firm*—Hoffmann & Baron

[57] ABSTRACT

A method and apparatus of determining the size of particles executing Brownian motion is provided. An integrated fiber optic probe, including a length of a gradient index multimode optical fiber fusion spliced to a monomode optical fiber, delivers laser light to a scattering medium such that the light scattered in the backward direction is collected by another integrated fiber optic probe mounted into the same cylindrical housing. The scattered light, after conversion to a series of photoelectron pulses, is processed to determine the mean particle diameter. The temporal coherence of the scattered field from submicroscopic particles illuminated by laser light is a function of both the integration time and the particle diameter. The temporal degree of coherence of the time averaged scattered intensity decreases as the integration time increases. Statistical processing of the scattered photons leads to a new method of particle sizing, which circumvents the need for digital autocorrelation.

23 Claims, 4 Drawing Sheets

METHOD AND APPARATUS FOR SUBMICROSCOPIC PARTICLE SIZING BY MEASURING DEGREE OF COHERENCE

The invention was made with Government support under contract no. NCC3-241 awarded by the National Aeronautics and Space Administration. The Government has certain rights in the invention.

BACKGROUND OF THE INVENTION

1. Field of the Invention

The field of the invention relates to integrated fiber optic based dynamic light scattering apparatus including an electronic processing system for the characterization of the size of the submicroscopic scatterers, including colloidal suspensions, polymers, and physiological structures such as proteins, a method of determining the size of such particles, and probes for detecting scattered light.

2. Brief Description of the Prior Art

Dynamic light scattering provides a temporal characterization of the scattering species executing Brownian motion; the scattering species are usually in the size range 3 nm to 3000 nm and can be colloidal particles, proteins, polymers or random phase fluctuations caused by density or temperature fluctuations. The technique requires coherent illumination and coherent detection from the scattering species. The accepted practice is to detect the scattered light as a series of photon events, which are processed using a real time digital correlator to yield an intensity autocorrelation. The intensity autocorrelation data, using suitable modeling, is inverted to yield a distribution of sizes or molecular weights. Correlation techniques have become the main stay of the state of art systems in use today. U.S. Pat. Nos. 4,975,237 and 4,983,040 disclose systems using correlation techniques for analyzing light scattered by particles undergoing Brownian motion. The photons streams may, however, be processed using equivalent spectral estimation techniques. Both techniques require several minutes of data acquisition followed by several minutes of data analysis prior to displaying the distribution of sizes.

The known systems for determining the mean diameter of particles exhibiting Brownian motion are relatively expensive, and require hardware which may be too large in size for certain field uses. Digital correlation which is the most often used approach for the experimental investigation of stochastic systems, requires an expensive piece of hardware in the correlator. Systems including such correlators further require computers having sufficient computing power to perform the necessary mathematical calculations. While the use of a PC or laptop computer in a lab or other convenient setting is not a problem, transporting such equipment to more inhospitable areas can be a significant drawback.

Probes employed for illuminating particles and/or detecting light scattered thereby have included several designs. In accordance with one probe embodiment shown in U.S. Pat. No. 5,155,549, both the transmitting and receiving fibers are coupled to a gradient index microlens. Such a microlens greatly increases the size of the probe, which may not be acceptable in certain circumstances. Alternative structures disclosed in the patent include a lensless probe, and one in which a microlens is formed on the end of the transmitting fiber either by dipping the fiber or by heating the fiber end such that the core thereof diffuses into the cladding. An integrated fiber optic probe used as a receiver of scattered light is disclosed in an article by Dhadwal et al., "Integrated fiber optic probe for dynamic light scattering", *Applied Optics* 32, 3901–3904 (1993). The probe includes a monomode fiber fusion spliced to a short length of graded-index multimode fiber. An unfocused, collimated laser beam was used to provide light to the sample cell.

SUMMARY OF THE INVENTION

It is an object of the invention to provide a method and apparatus for determining the size of particles exhibiting Brownian motion.

It is another object of the invention to provide a portable, relatively inexpensive apparatus for determining particle size, and a probe for use in such an apparatus.

A still further object of the invention is to provide a method and apparatus for determining mean particle diameter without the need for measuring the autocorrelation of scattered light and the hardware required for such measurement.

In accordance with such objects, an apparatus is provided which includes a laser source, means for processing scattered light into a series of photoelectron pulses, means for counting the number of pulses generated during specific integration times, means for storing pulse counts for a plurality of integration times, means for measuring the degree of coherence of the pulses for a plurality of values of integration time, and means for calculating the mean particle diameter from the degree of coherence of the pulses for said plurality of values of integration time. The apparatus further includes a probe for providing coherent detection of scattered light. The probe is coupled to the processing means. The laser source is also preferably coupled to the probe, such that the probe is used for both transmitting light and receiving scattered light from the fluid sample to be tested. With the exception of the probe, all of the components of the apparatus are preferably incorporated within a portable housing.

A method of determining the size of particles undergoing Brownian motion is also provided. The method includes the steps of providing a probe capable of providing self-beating detection of scattered light, illuminating a particle-containing fluid sample with a laser beam, causing the probe to receive light scattered by the particles in the fluid sample, converting said scattered light into a stream of voltage pulses, counting the number of pulses in a plurality of specified sample times, computing a continuous real time estimate of the average diameter of said particles based upon the degree of coherence during each sample time, and displaying the average diameter of said particles. The voltage pulses are preferably introduced to a front end gated counting system, with subsequent stages to provide photon count data at a plurality of gate times.

DETAILED DESCRIPTION OF THE INVENTION

Figure 1:
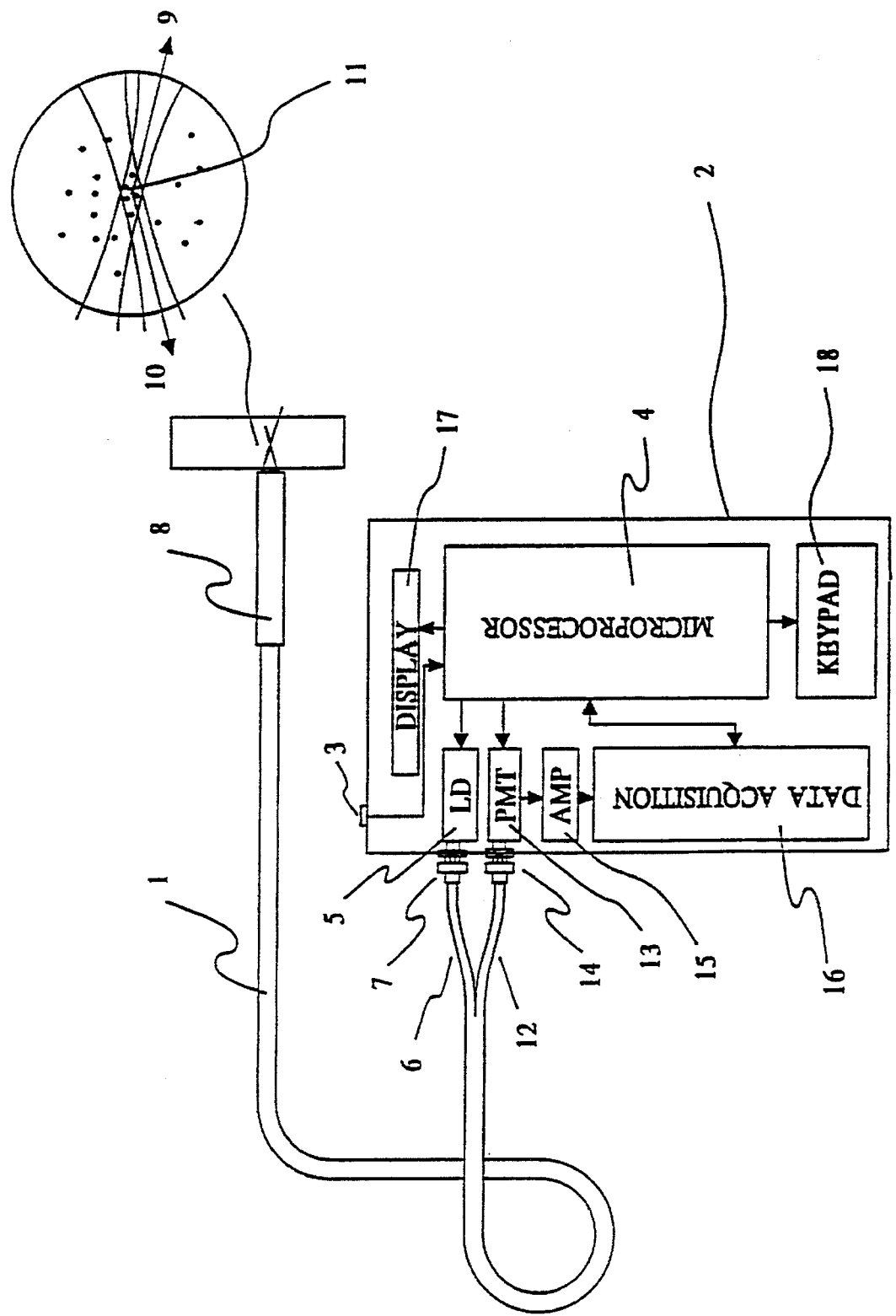
FIG. 1 is a schematic of a portable particle sizing system according to the invention.

The present invention concerns a method and apparatus for determining the size of particles exhibiting Brownian motion, and a probe capable of use in such an apparatus.

Brownian motion and potential theory are terms used to describe many physical phenomena in which some physical quantity (or mathematical variable) is continuously undergoing random (or stochastic) fluctuations. These phenomena have been extensively studied since first reported in 1828 by its discoverer, Robert Brown. Brownian motion is an outward manifestation of molecular motion as predicted by Albert Einstein in 1905 and experimentally verified by Jean Perrin in 1909. Today, Brownian motion is utilized to describe countless diffusion processes occurring in many diverse disciplines ranging from the motion of electrons and holes in semiconductors devices, to the motion of molecules and colloids in chemistry, to the motion of bacteria and viruses in biology, to the diffusion of pollutants in the atmosphere. Diffusion processes in fluids have captured the attention of experimental physicists, engineers, chemists and biologists. In particular, with the advent of the laser and sophistication in the microelectronics industry, dynamic light scattering (DLS) or photon correlation spectroscopy (PCS) techniques have become indispensable non-invasive diagnostic tools for probing chemical and biological systems. DLS provides information on the temporal properties of the scattered field, which for Brownian motion, after appropriate processing, gives the distribution of diffusion coefficients.

DLS utilizes the temporal fluctuations of the scattered light intensity to investigate the dynamic behavior of fluid systems; PCS is synonymous with DLS, except for the use of photons. The doubly stochastic scattered photons are mostly processed using correlation techniques. However, other alternative signal processing techniques such as the structurator, amplitude weight phase spectrum, and spectral estimation are useful under certain circumstances. In a typical PCS experiment, the scattered intensity is detected as a stream of photons and the number of photon events in a time interval T is $n_T(t)$. For Gaussian signals the photon count (intensity) autocorrelation can be related to the normalized electric field autocorrelation $g^{(1)}(\tau)$ by the Siegert relation $$G^{(2)}(\tau) = N_S \langle n_T(t) n_T(t+\tau) \rangle = N_S \langle n_T \rangle \delta(\tau) + N_S \langle n_T \rangle^2 [1 + \beta |g^{(1)}(\tau)|^2] \quad (1)$$

where $N_S$ is the total number of samples, $\tau$ is the delay time increment, usually expressed as an integer multiple of T, $\langle n_T \rangle$ is the average count per sample time, and $\beta$ is the degree of coherence of the scattered optical field. In DLS the degree of coherence is typically identified with the number of independent speckles in the detector aperture, and has an ideal value of unity. The degree of coherence can be separated into two components, a spatial coherence part $\beta_S$ and a temporal coherence part $\beta_t$. In DLS, the integration time (or in some cases the sampling time) is usually much smaller than the characteristic decay time of the diffusive motion, and subsequently $\beta_t$ is close to its ideal value of unity. Under this assumption all observed changes in the overall $\beta$ ($=\beta_S \beta_t$) are due to geometric considerations of the detector configuration, and $\beta$ is the so-called spatial coherence factor. A long integration time is normally used to mask the effects of Brownian motion in order to study the static properties of the scattered light ($\beta_t=0$). Note that equation (1) is valid only for the self-beating experiment. $G^{(2)}(\tau)$ decays from an initial value of $N_S \langle n_T^2 \rangle$ to a baseline of $N_S \langle n_T \rangle^2$. The function $g^{(1)}(\tau)$, which has an initial value of 1 and decays to zero at $\tau=\infty$, is a function of the characteristic line width distribution $G(\Gamma)$. In the absence of directed particle motion, the electric field autocorrelation is a Laplace transform of $G(\Gamma)$, the distribution of characteristic line widths, that is, $$g^{(1)}(\tau) = \int_0^\infty G(\Gamma) \exp(-\Gamma \tau) d\Gamma \quad (2)$$

where, $$\Gamma = Q^2 D_o = \frac{16 n_m^2 \pi^2}{\lambda_o^2} \sin^2\left(\frac{\theta}{2}\right) \frac{k_B T_\theta}{3\pi \eta d}$$

Q is the magnitude of the Bragg wave vector, $n_m$ is the refractive index of the medium, $\lambda_o$ is the wavelength of light in vacuum, $\theta$ is the scattering angle, $D_o$ is the translational diffusion coefficient of a dilute suspension spherical particles of diameter d, $k_B$ is Boltzman's constant, $T_\theta$ and $\eta$ are the absolute temperature, and viscosity of the medium, respectively. The inversion problem in PCS is that of recovering $G(\Gamma)$ from measured data that has been reduced to give a noisy estimate $g^{(1)}(\tau)$. Subsequent scaling and computations of the scattering amplitudes gives an equivalent distribution of particle size.

In accordance with the present invention, the integration time or sampling time is varied for the purpose of devising new signal processing techniques for studying Brownian motion. As outlined below, the degree of coherence is a function of the mean particle diameter and the integration time. Therefore, a measurement of the temporal degree of coherence of the scattered photons is equivalent to a direct measurement of the particle size.

The study of photon counting statistics has a long history, dating back to the 1950s, when the possibility of calculating the fluctuation of the number of photons by associating the photons stochastically with Gaussian random waves of the appropriate spectral distribution was predicted and later confirmed through experimentation. The statistics of intensity fluctuations from a Gaussian light source with a Lorentzian spectrum, once derived, was extended by Slepian to include the statistics of Gaussian white noise passing through an RC filter, and was applied to light scattering by Jakeman and Pike. D. Slepian, "Fluctuations of Random Noise Power", *The Bell System Technical Journal*, pp. 163–184, January 1958; E. Jakeman and E. R. Pike, "The Intensity-Flactuation Distribution of Gaussian Light", *J. Phys. A.*, 1968, Ser. 2, Vol. 1, pp. 128–138. Consequently, the relationships between the moments of scattered photon counts and of intensity fluctuations are well established, under the assumption that the detection area is small enough to permit efficient self-beating.

As discussed above, the conventional approach for the experimental investigation of stochastic systems, in particular, Brownian motion, utilizes either correlation or spectral estimation techniques; the field of DLS uses mostly digital correlation techniques. The present invention concerns a direct method of particle sizing based on the statistical processing of photons, and an apparatus which makes use of the method in a unique manner to quickly and accurately provide such data. Previous attempts have failed to establish the utility of using photon counts as a direct means of particle sizing. Results of simulations and experiments show that the direct method of processing photon counts is reliable and accurate. The distribution of photoelectron pulses arising from a detector illuminated by a coherent light of constant intensity I follows a Poisson process, $$p(n_T,t) = \frac{\mu^{n_T}}{n_T!} \exp(-\mu)$$

where $$\mu = \alpha \int_t^{t+T} I(\xi)d\xi = \alpha IT$$

$\alpha$ is the quantum efficiency of the detector, and $n_T$ is the number of photon events in the integration time T. In most cases of interest the scattered intensity I(t) is a continuous stochastic process with a probability density $p(I_s)$, where is a random variable, $$I_s = \int_t^{t+T} I(\xi)d\xi$$

Subsequently, the resulting photon counting distribution becomes $$p(n_T) = \left(\frac{(\alpha I_s)^{n_T}}{n_T!} \exp(-\alpha I_s)\right)_{I_s} = \int_0^\infty \frac{(\alpha I_s)^{n_T}}{n_T!} \exp(-\alpha I_s)p(I_s)dI_s$$

where $\langle\rangle$ denotes the ensemble average over the $I_s$ distribution. As a result, the photon counting fluctuation is a doubly stochastic process. In the study of photon counting statistics it is convenient to consider the factorial moments of photon counts $$\left(\frac{n_T!}{(n_T-m)!}\right) = \langle n_T(n_T-1)\ldots(n_T-m+1)\rangle = \sum_{n_T=0}^\infty n_T(n_T-1)\ldots(n_T-m+1)p(n_T)$$

where $n_T$ is the photon count and m is the degree of factorial moments. The resulting factorial moments are directly related to $I_s$ as $$\langle n_T(n_T-1)\ldots(n_T-m+1)\rangle = \alpha^m \langle I_s^m\rangle$$

where, $$\langle n_T\rangle = \alpha\langle I_s\rangle$$

and $$\langle n_T(n_T-1)\rangle = \langle n_T^2\rangle - \langle n_T\rangle = \alpha^2\langle I_s^2\rangle$$

Therefore, the variance in $n_T$ can be easily derived as $$\sigma_{n_T}^2 = \langle n_T^2\rangle - \langle n_T\rangle^2 = \langle n_T\rangle + \alpha^2(\langle I_s^2\rangle - \langle I_s\rangle^2) = \langle n_T\rangle + \alpha^2\sigma_{I_s}^2 \quad (3)$$

The above equation shows that the variance of the photon counts comprises two independent parts; the variance due to the random generation of photons obeying Poisson statistics ($\langle n_T\rangle$ part), and the variance of the intensity fluctuations ($\alpha^2 \sigma_{I_s}^2$ part). Thus, it is possible to determine the statistics of intensity fluctuations from the statistics of photon counts. The most important feature of the intensity distribution $p(I_s)$ is its variance, which can be predicted from known analysis of noise processes. The variance of the scattered light is given by:

$$\sigma_{I_s}^2 = \frac{\langle I_s\rangle^2}{2\gamma^2}[\exp(-2\gamma) + 2\gamma - 1]$$

where $\gamma=\Gamma T$. One important assumption made for the derivation of the above equation is that the detector area is sufficiently small such that the variation of intensity over the detector area is negligible, that is, that $\beta_s \approx 1$. In actual experiments, however, this may not be true.

In the limit $\tau \to 0$ equation (1) becomes $$\sigma_{n_T}^2 = \langle n_T\rangle + \langle n_T\rangle^2\beta$$

Equating with equation (3) gives $$\langle n_T\rangle^2\beta = \alpha^2\sigma_{I_s}^2$$

The variance in the scattered intensity is proportional to $\beta$. Combining the above equations gives $$\beta(T) = \frac{\sigma_{n_T}^2 - \langle n_T\rangle}{\langle n_T\rangle^2} = \frac{\langle n_T^2\rangle - \langle n_T\rangle^2 - \langle n_T\rangle}{\langle n_T\rangle^2} = \frac{\beta_s}{2(\Gamma T)^2}[\exp(-2\Gamma T) + 2\Gamma T - 1] \quad (4)$$

which shows that $\beta$ is a function of T, the integration time, and $\Gamma$, which is related to the mean particle diameter through the Stokes-Einstein relation given earlier, equation(2). Therefore, the mean particle diameter can be recovered by measuring the degree of coherence of the scattered photons as a function of the integration time. The validity of equation (4) has been tested using a specially designed Brownian motion simulator and a conventional PCS apparatus. The results are summarized in Tables 1 and 2 for a range of particle sizes and at several different scattering angles.

3. Computation of Particle Diameter Based on two estimates of $\beta(T)$

The particle diameter d is computed from an estimate of $\Gamma$, which can be obtained by measuring $\beta(T)$ at a few logarithmically spaced values of T, covering the range of $\Gamma T$ from 0 to about 10. A portable sizing system must, however, be computationally less intensive. Under certain approximation a reasonably good estimate of $\Gamma$ can be obtained by measuring $\beta(T)$ at two integration times T and KT. T and K are chosen such that a reasonable range in particle size can be covered, with the fastest available electronics. With T=200 ns and K=25, particles with diameters in the range 5 nm to 3000 nm can be detected without any changes in the integration times. Equation (2) can be expressed as polynomial expansion $$\beta(T) = 2\beta_s\left[1 - \frac{(2\Gamma T)}{3!} + \frac{(2\Gamma T)^2}{4!} + \frac{(2\Gamma T)^3}{5!} + \cdots\right]$$

which gives two approximations:

$$\beta(T) = \beta_s\left[1 - \frac{2}{3}\Gamma T\right], \Gamma T < 0.1$$

and $$\beta(T) = \beta_s\left[1 - \frac{2}{3}\Gamma T + \frac{1}{3}(\Gamma T)^2\right], 0.1 < \Gamma T < 0.5$$

Two estimates $\beta(T)$, that is $\beta_1 = \beta(T)$, and $\beta_2 = \beta(KT)$, can be computed from a measurement of the photon events using either a single counter or using two separate counters. In either case $\Gamma$ can be estimated using the following two equations $$\Gamma = \frac{3}{2KT} \left[ 1 - \frac{\beta_2}{\beta_1} \right], \Gamma T < 0.1 \quad (5)$$

$$\Gamma = \frac{1}{KT} \left[ 1 + \sqrt{3 \frac{\beta_2}{\beta_1} - 2} \right], 0.1 < \Gamma T < 0.5 \quad (6)$$

FIG. 1 shows a compact, hand-held system which provides particle size information in a few seconds compared with a few minutes for the desktop-based, state of the art PCS systems currently in use. The system includes an integrated back scatter fiber optic probe (IBFOP) 8 and an electronic processing package or housing 2 occupying a volume of about 6"×4"×2". Two hardware implementations are disclosed herein: the first is based upon acquiring and storing one million samples prior to processing by the microprocessor, while the second is based upon continuous processing of the photon streams. The former implementation permits more user interaction and has the ability to reprocess the same data in a number of different ways. However, the latter scheme is more suitable for rapid determinations of particle size.

The apparatus includes the housing 2, which incorporates substantially all of the necessary components for determining particle size, and a probe 8 coupled to the housing by a cable 1.

A microprocessor 4 is provided for controlling the acquisition of date by means of the probe, the processing of the photons detected by the probe, the analysis of the processed photons, and the display of the desired physical properties of the particles in the sample.

A laser source 5 is mounted to the housing and coupled to the microprocessor. The laser source may include a visible laser diode, and is used as a coherent light source necessary for successfully employing the apparatus according to the invention. The probe 8 is coupled to the laser diode, and is capable of emitting light received therefrom. The laser source is also coupled to the microprocessor 4, which controls the operation thereof.

A cable 1 including first and second optical fibers is connected to the probe. The laser diode is connected to one of the two fibers, which shall be referred to as the transmitting fiber. The transmitting fiber is preferably a monomode fiber. The probe and cable may be substantially as shown and described in U.S. Pat. No. 5,155,549, which is incorporated by reference herein. The transmitting fiber may be lensless, or coupled to a lens as described with respect to several of the embodiments of U.S. Pat. No. 5,155,549. A short length of gradient index multimode optical fiber may, however, be fusion spliced to the end of the monomode fiber for delivering the light to the scattering medium as described below. The use of such a splice is preferred.

The fiber optic probe, which includes a transmitting fiber 6, and one or more receiving fibers 12, is positioned inside or outside a scattering chamber which contains the scattering medium. The probe delivers light from a semiconductor (laser diode) or other source of laser light, and coherently detects the light scattered by particles in the medium in the backward direction. The light is detected at one or more pre-defined scattering angles.

A photomultiplier 13 or avalanche photodiode is incorporated within the housing, and coupled to the receiving fiber(s) 12 by a FC/PC bulkhead adapter 14. A similar adapter 7 is used to couple the transmitting fiber 6 to the laser source 5. The photomultiplier is controlled by the microprocessor and converts the scattered photons into a stream of voltage pulses, which are processed by an amplifier/discriminator 15.

A data acquisition module 16 is connected to the amplifier/discriminator. The module preferably includes a front end gated counter 19 capable of real time operation in the sub-microsecond regime, with subsequent stages to provide photon count data at several gate times. Contiguous counts for every sample time are loaded into a static random access memory (SRAM) 20, which is also incorporated within the module. (See FIG. 2a).

The particle size measurement is initiated by a user prompt via a start switch 3. The microprocessor 4 controls the entire functioning of the system through programmed instructions stored in its internal memory registers. The first task enables the laser diode 5 for a preset duration time. The laser light emanating from the integrated fiber optic probe tip (IFOP) illuminates the scattering medium with a tightly focussed laser beam 9 having a diameter, typically, less than 100 μm. Light scattered, in the backward direction 10, by submicroscopic particles 11 is collected by a second IFOP which is mounted in same probe body. The scattered light is transmitted by the second optical fiber 12 to the photomultiplier 13 via the FC/PC bulk head adapter 14. The photomultiplier converts the scattered photons into a stream of current pulses, which are processed into a stream of equal amplitude voltage pulses by the amplifier/discriminator 15; the scattered intensity is proportional to the rate of these voltage pulses which have random arrival times. The data acquisition module 16 processes these random voltage pulses according to the statistical rules outlined above. The data acquisition module is controlled by the microprocessor which also computes the particle diameter and outputs the value to a liquid crystal display 17. A keypad 18 permits user input to the microprocessor. Two possible hardware implementation of the data acquisition are disclosed.

Figure 2A:
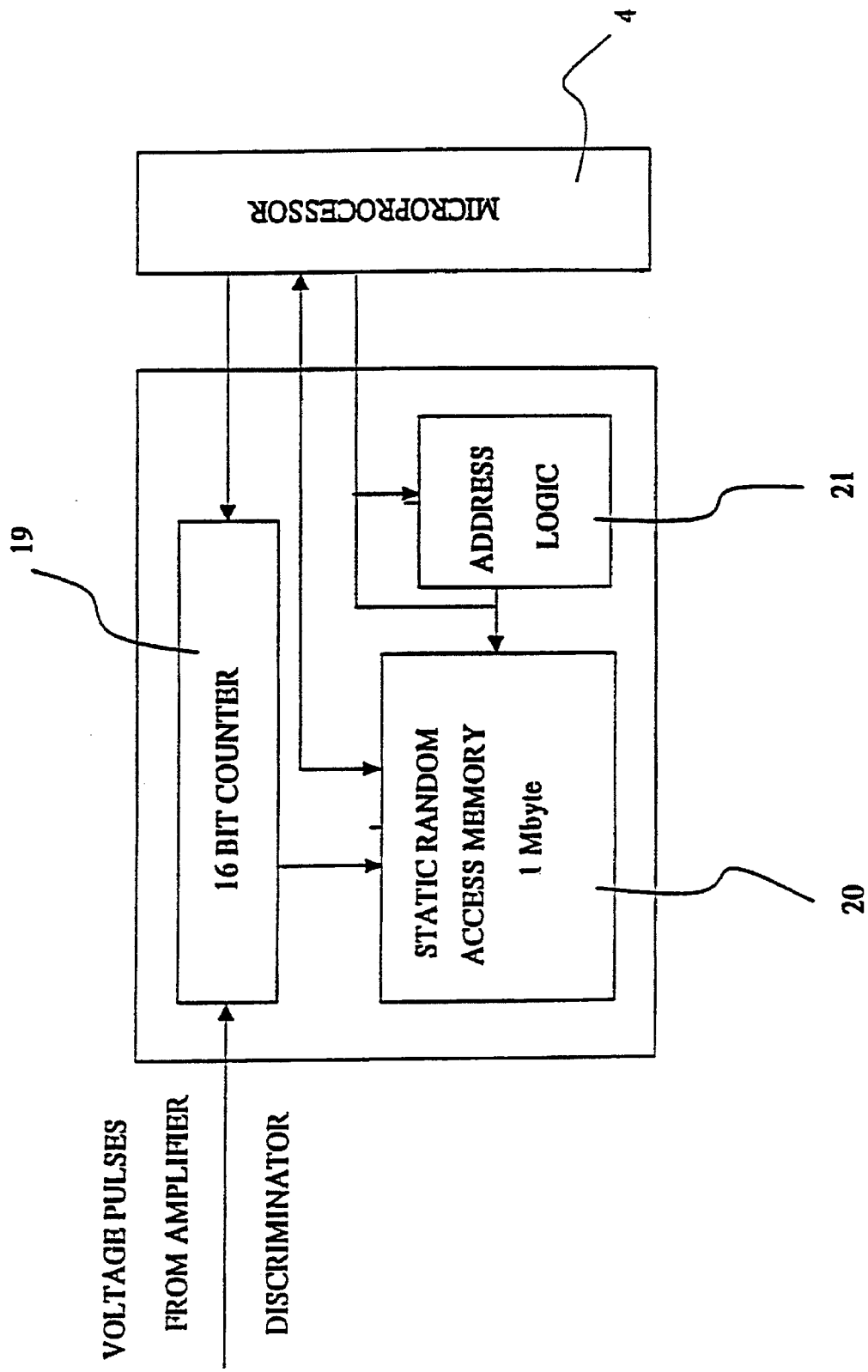
FIG. 2a is a schematic of a first data acquisition system according to the invention.

The first data acquisition module, shown in FIG. 2a, counts the number of photon events $n_T$ occurring in a time interval T using a 16-bit counter 19. The output of the counter is stored in a one megabyte static random access memory 20. The address generating logic 21 and the sampling interval are generated by the microprocessor 4. Additionally, the time interval can be set by the user through a key pad 18. At the end of the data acquisition cycle, the microprocessor disables the laser diode and photomultiplier from acquiring further data. The system switches into the signal processing mode in which the data stored in the SRAM are manipulated according to the following equations in order to compute $\beta_1$ and $\beta_2$ using equation (4)

$$<n_T> = \frac{1}{N_s} \sum_{i=1}^{N_s} n_{Ti}$$

$$<n_T^2> = \frac{1}{N_s} \sum_{i=1}^{N_s} n_{Ti}^2$$

$$<n_{KT}> = K<n_T>$$

$$<n_{KT}^2> = \frac{K}{N_s} \sum_{i=1}^{\frac{K}{K}} \left[ \frac{1}{K} \sum_{j=K(i-1)+1}^{Ki} n_{Tj} \right]^2$$

Subsequently equations (5), (6), and (2) are used to estimate the average particle diameter, which is displayed to the user via an appropriate display 17.

Figure 2B:
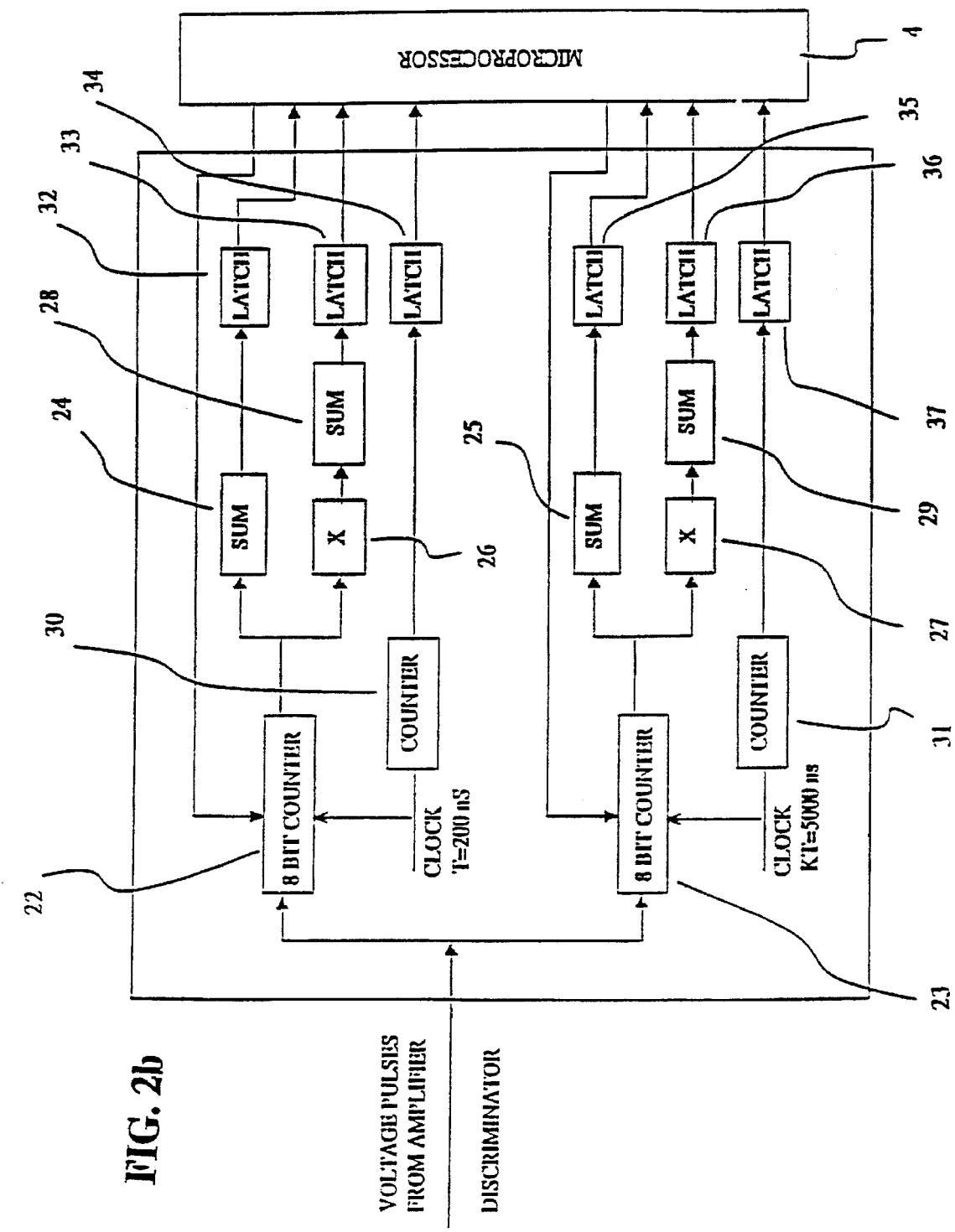
FIG. 2b is a schematic of a second data acquisition system according to the invention.

The second hardware implementation of the data acquisition block is shown in FIG. 2b. The voltage pulses from the amplifier/discriminator are simultaneously directed to the inputs of two 8-bit counters 22 and 23; these two counters measure the photon events $n_T$ and $n_{KT}$ in time intervals of T=200 ns and KT=5000 ns, respectively. The output of the counters is simultaneously clocked into accumulators 24 and 25, and 8-bit multipliers 26 and 27. The total counts $\Sigma n_T$, and, $\Sigma n_{KT}$ are stored in accumulators 24 and 25. The total counts $\Sigma n_T^2$, and, $\Sigma n_{KT}^2$ are stored in accumulators 28 and 29. Counters 30 and 31 keep a running total of the number of the total samples $N_1$ ($\equiv N_S$) and $N_2$ ($\equiv N_S/K$), respectively. The microprocessor 4 periodically, say every 500 ms, polls the latches 32, 33, 34, 35, 36, and 37 to read values of $\Sigma n_T$, $\Sigma n_T^2$, $N_1$, $\Sigma n_{KT}$, $\Sigma n_{KT}^2$, and $N_2$. These values are used to compute $\beta_1$, $\beta_2$ and $\Gamma$ using equation (4). Subsequently the particle diameter is computed using equation (2). The particle diameter is displayed and updated every 500 ms. An accurate estimate (within 4%) is available within about two seconds. In this configuration, no user input is required. Physical properties of certain standard mediums can be stored in the registers of the microprocessor. The data acquisition module continues to process the photon stream until either a reset from the user or until the accumulator full flag goes up.

Figure 3A:
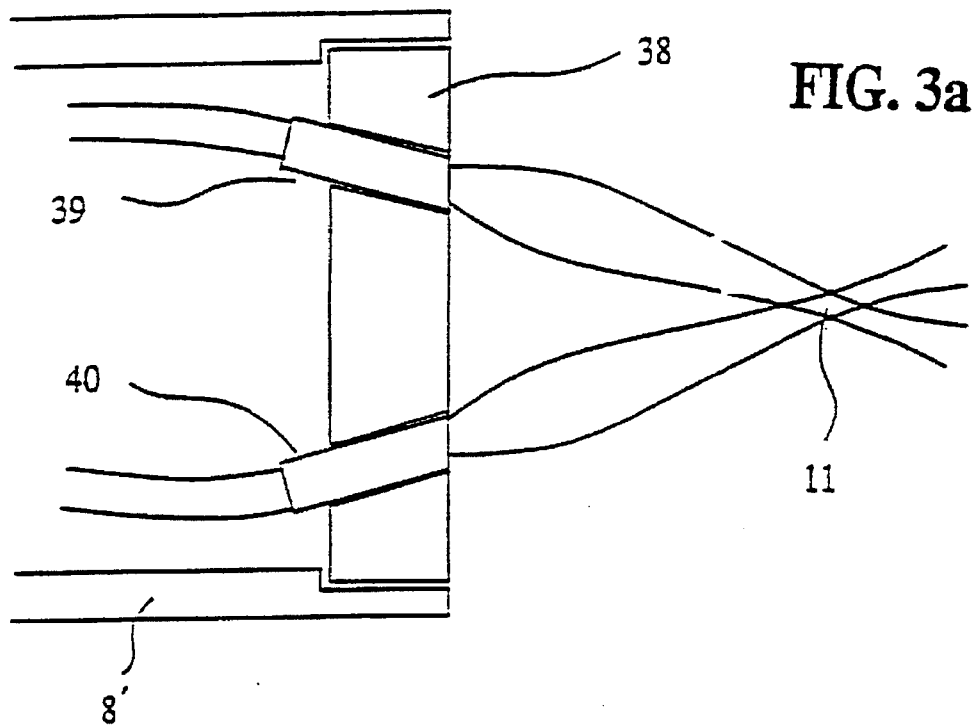
FIG. 3a is a schematic of a portion of an integrated back scatter fiber optic probe.

An IBFOP 8, shown in FIG. 3a, is similar to the back scattering fiber-optic probe (BFOP) disclosed in U.S. Pat. No. 5,155,549 only in the physical arrangement of the transmitting and receiving fibers in the face plate 38. The BFOP probe uses a monomode optical fiber to deliver a diverging laser beam to the scattering medium and a second optical fiber for receiving the scattered light. There are many situations which require delivery of a focussed laser beam, either for higher power density or for higher spatial resolution. Conventional means of modifying the BFOP to achieve a focussed delivery system is impractical because of the increased sensitivity to alignment and an unacceptable increase in the size of the BFOP. The smallest, commercially available, gradient index lens increases the diameter of the probe by one order of magnitude.

The IBFOP 8 comprises two IFOPs 39 and 40 which are mounted into precisely drilled holes in a stainless steel face plate 38, which is mounted into a cylindrical housing 8. One IFOP delivers a focussed laser beam to the scattering region 11; the second IFOP detects the scattered light in some backward direction, typically, 150°. The IFOP is fabricated by fusion splicing a plurality of different multimode fibers to a monomode fiber. For the IFOP in FIG. 3b, a gradient index multimode fiber 41 is fusion spliced to a step index multimode fiber 42, which is fusion spliced to a monomode fiber 43. The two multimode fibers are cleaved to the correct length (about 283 µm) using a high magnification optical microscope. The IFOP is then epoxied into a stainless steel tubing 44 of the appropriate diameter, and the resulting IFOP is epoxied into the face plate 38. The IBFOP requires no alignment and can be custom designed for any spot size requirements in the scattering region, which can be inside odd shaped and inaccessible container in remote locations. The monomode fiber may have a core radius of 2 µm and a mode field radius of 2.3 µm, with a cladding diameter of 125 µm.

Figure 3B:
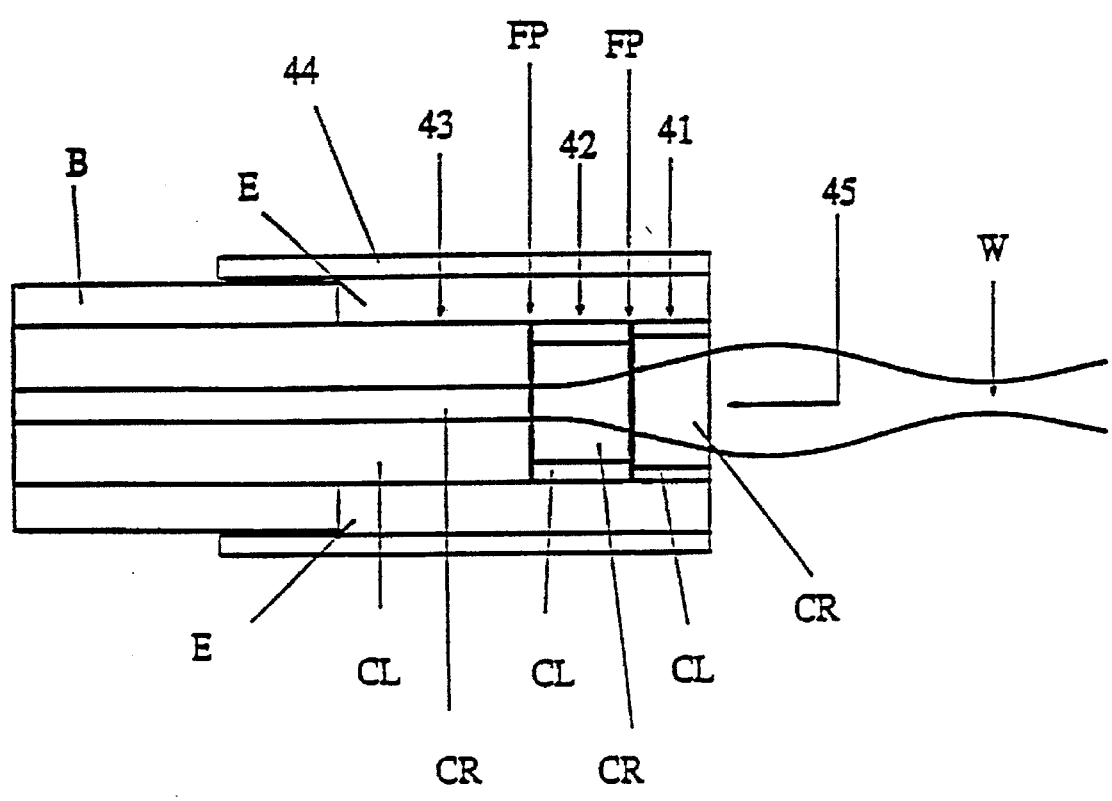
FIG. 3b is a schematic of an integrated fiber optic probe, wherein CR designates the core region of optical fiber, CL the cladding region of optical fiber, FP the fusion splice regions, B a buffer coating of optical fiber, E an epoxy, and W the focussed region of the transmitting fiber.

As shown in FIG. 3b, the transmitting IFOP achieves the desired focusing through an innovative use of fusion splicing of short sections of step index and gradient index multimode fibers to a single monomode fiber. The step index optical fiber acts like a spacer while the gradient index optical fiber provides a focussing effect, depending upon its length. The cladding diameters of both multimode fibers approximate that of the monomode fiber. The IFOP configuration allows one to engineer the wavefront of the laser beam emanating from the tip of a monomode optical fiber into any arbitrary shaped wavefront without leaving the optical fiber until the final surface 45.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

TABLE 1

Comparison of the results obtained using simulated Brownian motion data from an aqueous suspension of polystyrene latex spheres (PLS).

| PLS Sample | Scattering | Line width Estimate, $\Gamma$ (s$^{-1}$) | | |
|---|---|---|---|---|
| Nominal Diameter (nm) | Angle (degrees) | Expected | PCS with $T_D = 60s$ | Direct Method $T_D = 20s$ |
| 17 | 90 | 9569.5 | 9295.2 | 9414 |
| 42 | 90 | 3873.4 | 3394.5 | 3657 |
| 85 | 90 | 1914.9 | 1906 | 1888 |
| 170 | 90 | 957 | 1137 | 1100 |
| 85 | 30 | 256.4 | 283.2 | 204 |
| 85 | 45 | 560.6 | 598 | 622 |
| 85 | 60 | 957 | 917 | 634 |
| 85 | 75 | 1418.5 | 1264 | 1578 |
| 85 | 90 | 1913.9 | 1906 | 1888 |
| 85 | 105 | 2409.2 | 3153 | 2568 |
| 85 | 120 | 2870.8 | 3337 | 2568 |
| 85 | 135 | 3267.2 | 3371 | 2993 |
| 85 | 150 | 3571.4 | 3134.4 | 2853 |

TABLE 2

Summary of the experimental results for 85 nm PLS suspended in water

| PLS Sample | Scattering | Line width Estimate, $\Gamma$ (s$^{-1}$) | | |
|---|---|---|---|---|
| Nominal Diameter (nm) | Angle (degrees) | PCS with $T_D = 60s$ | PCS with $T_D = 20s$ | Direct Method $T_D = 20s$ |
| 85 | 60 | 880.8 | 898 | 919 |
| 85 | 90 | 1708.5 | 1717.7 | 1667.6 |
| 85 | 120 | 2467.4 | 2500.8 | 2432.3 |
| 18 | 60 | 3341.9 | 3362 | 3191.4 |
| 18 | 90 | 6300.2 | 6310.4 | 6122 |
| 18 | 120 | 9144.7 | 9172.8 | 8828.9 |

What is claimed is:

1. An apparatus for submicroscopic particle sizing, comprising:

a laser source;

means for coherently detecting scattered light;

means for processing scattered light detected by the detecting means into a series of photoelectron pulses;

means for counting the number of photoelectron pulses generated during a plurality of specified integration times;

means for storing pulse counts for a plurality of integration times;

means for measuring the degree of coherence of the pulses for a plurality of values of integration time, and means for calculating the mean particle diameter from the degree of coherence of the pulses for said plurality of values of integration time, whereby submicroscopic particle sizing is accomplished without the use of photon correlation means or spectral estimation means.

2. An apparatus as described in claim 1 wherein said means for coherently detecting scattered light includes a probe connected to said means for processing and to said laser source.

3. An apparatus as described in claim 2 wherein said probe includes a gradient index multimode optical fiber having an exposed end face for transmitting and focussing light from said laser source, said probe being connected to said laser source by a monomode fiber.

4. An apparatus as described in claim 3 including spacing means connected between said monomode fiber and said gradient index microlens.

5. An apparatus as described in claim 1 wherein said counting means is a front end gated counter capable of real time operation in the sub-microsecond regime, and having subsequent stages to provide photon count data at a plurality of gate times.

6. An apparatus as described in claim 5 wherein said means for storing is a static random access memory connected to said counter.

7. An apparatus as described in claim 1 wherein said counting means includes a plurality of counters, each of said counters being capable of measuring photon events in a different time interval.

8. An apparatus as described in claim 7 wherein said means for storing includes a first plurality of accumulators connected, respectively, to said counters.

9. An apparatus as described in claim 8 including a plurality of multipliers connected, respectively, to said counters, and a second plurality of accumulators connected, respectively, to said multipliers.

10. An apparatus as described in claim 9 including a plurality of latches connected, respectively, between each of said first and second plurality of accumulators and a microprocessor.

11. An apparatus as described in claim 7 wherein said means for processing is an amplifier/discriminator connected to each of said counters.

12. An apparatus as described in claim 11 including clock means for controlling the sampling time of the respective counters.

13. An apparatus as described in claim 2 including a portable housing, said laser source, means for processing, means for counting, means for storing, means for measuring and means for calculating all being incorporated within said portable housing.

14. An apparatus as described in claim 13 wherein said portable housing includes a display connected to a microprocessor.

15. An apparatus as described in claim 14 including a keypad incorporated within said housing for providing input to said microprocessor.

16. A method of determining the size of particles undergoing Brownian motion, comprising:
    providing a probe capable of providing self-beating detection of scatter light;
    illuminating a particle-containing fluid sample with a laser beam;
    causing the probe to coherently detect light scattered by the particles in the fluid sample;
    converting said scattered light into a stream of electrical pulses;
    counting the number of pulses in a plurality of specified sample times;
    determining the degree of coherence of the scattered light during each of said sample times, and
    computing an estimate of the average diameter of said particles based upon the degree of coherence during each of said sample times.

17. A method as described in claim 16 including the steps of storing the pulses, discontinuing counting said pulses, and thereafter determining the degree of coherence of the scattered light during said plurality of sample times.

18. A method as described in claim 17 wherein the degree of coherence is determined at two sample times T and KT.

19. A method as described in claim 18 wherein K is about 25 and T is about 200 ns.

20. A method as described in claim 16 including the step of processing said pulses into a stream of equal amplitude pulses prior to counting the number of such pulses.

21. A method as described in claim 16 including the step of simultaneously directly said pulses to a plurality of counters, and causing said counters to count, respectively, said pulses during said plurality of sample times.

22. A method as described in claim 21 including simultaneously clocking the output of said counters into a plurality of first accumulators and multipliers, causing a plurality of second accumulators to store the outputs of said multipliers, and determining the degree of coherence of said scattered light from the outputs of said first and second accumulators.

23. A method as described in claim 16 including the step of focusing said laser beam within said fluid sample.

* * * * *